United States Patent
Igarashi et al.

(10) Patent No.: US 11,000,184 B2
(45) Date of Patent: May 11, 2021

(54) IMAGE PICKUP MODULE, FABRICATION METHOD FOR IMAGE PICKUP MODULE, AND ENDOSCOPE

(71) Applicant: OLYMPUS CORPORATION, Tokyo (JP)

(72) Inventors: Takatoshi Igarashi, Hachioji (JP); Takahiro Shimohata, Shiojiri (JP); Takuro Suyama, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 91 days.

(21) Appl. No.: 16/656,788

(22) Filed: Oct. 18, 2019

(65) Prior Publication Data
US 2020/0049972 A1 Feb. 13, 2020

Related U.S. Application Data

(63) Continuation of application No. PCT/JP2018/015774, filed on Apr. 16, 2018.

(30) Foreign Application Priority Data

Apr. 19, 2017 (WO) .................. PCT/JP2017/015662

(51) Int. Cl.
*A61B 1/005* (2006.01)
*A61B 1/05* (2006.01)
(Continued)

(52) U.S. Cl.
CPC .......... *A61B 1/051* (2013.01); *A61B 1/00006* (2013.01); *A61B 1/00009* (2013.01);
(Continued)

(58) Field of Classification Search
CPC ... A61B 1/00018; A61B 1/0011; A61B 1/051; H01L 27/14636
See application file for complete search history.

(56) References Cited

U.S. PATENT DOCUMENTS 7,828,736 B2 * 11/2010 Tanaka .................. B06B 1/0622
 600/459
2004/0130640 A1 7/2004 Fujimori
(Continued)

FOREIGN PATENT DOCUMENTS

EP 1577950 A1 9/2005
EP 3053508 A1 8/2016
(Continued)

OTHER PUBLICATIONS

International Search Report dated Jun. 26, 2018 issued in PCT/JP2018/015774.

*Primary Examiner* — Daniel Chang
(74) *Attorney, Agent, or Firm* — Scully, Scott, Murphy & Presser, P.C.

(57) ABSTRACT

An image pickup module includes a stacked element in which an external electrode is disposed on a rear surface, a first wiring board where a front electrode connected to the external electrode by an interconnecting bonding section and a first electrode are disposed, and a first signal cable connected to the first electrode by a cable bonding section, in which the first wiring board is flexible and includes a bent section in a space defined by extending a first region out of the first region and a second region obtained by dividing the rear surface into two regions in an optical axis direction, and a length of the first wiring board from the interconnecting bonding section to the cable bonding section is longer than a length of the stacked element from the interconnecting bonding section to an end side in the first region.

13 Claims, 6 Drawing Sheets

(51) Int. Cl.
  *A61B 1/00* (2006.01)
  *G06T 7/00* (2017.01)
  *G02B 23/24* (2006.01)
  *H01L 27/146* (2006.01)
  *H04N 5/225* (2006.01)
  *A61B 1/06* (2006.01)

(52) U.S. Cl.
  CPC ...... *A61B 1/00018* (2013.01); *A61B 1/00096* (2013.01); *G02B 23/2423* (2013.01); *G02B 23/2484* (2013.01); *G06T 7/0012* (2013.01); *H01L 27/14636* (2013.01); *H04N 5/2253* (2013.01); *A61B 1/0684* (2013.01)

(56) References Cited

U.S. PATENT DOCUMENTS

| | | |
|---|---|---|
| 2006/0249737 A1 | 11/2006 | Fujimori |
| 2011/0249106 A1 | 10/2011 | Makino et al. |
| 2011/0270179 A1* | 11/2011 | Ouyang ............. A61B 1/00062 604/110 |
| 2015/0357300 A1* | 12/2015 | Saito ....................... H01L 24/13 257/737 |
| 2016/0209637 A1 | 7/2016 | Fujimori |
| 2017/0025372 A1* | 1/2017 | Kojima ............... H01L 23/4985 |
| 2017/0171488 A1* | 6/2017 | Oike ....................... H04N 5/341 |
| 2017/0215699 A1* | 8/2017 | Ouyang ............. A61B 1/00062 |
| 2018/0026068 A1* | 1/2018 | Ogi ................... H01L 27/14636 257/432 |
| 2018/0041671 A1 | 2/2018 | Fujimori |
| 2018/0226441 A1* | 8/2018 | Kondo ................... H04N 5/378 |

FOREIGN PATENT DOCUMENTS

| | | |
|---|---|---|
| JP | 2004-207461 A | 7/2004 |
| JP | 2005-334509 A | 12/2005 |
| JP | 2009-082503 A | 4/2009 |
| JP | 2012-064883 A | 3/2012 |
| JP | 2013-030593 A | 2/2013 |
| JP | 2015-508299 A | 3/2015 |
| JP | 2015-066297 A | 4/2015 |
| WO | WO 2004/059740 A1 | 7/2004 |
| WO | WO 2009/041724 A1 | 4/2009 |
| WO | WO 2015/045630 A1 | 4/2015 |
| WO | WO 2016/166890 A1 | 10/2016 |

* cited by examiner

IMAGE PICKUP MODULE, FABRICATION METHOD FOR IMAGE PICKUP MODULE, AND ENDOSCOPE

CROSS REFERENCE TO RELATED APPLICATION

This application is a continuation application of PCT/JP2018/015774 filed on Apr. 16, 2018 and claims benefit of PCT/JP2017/015662 filed in Japan on Apr. 19, 2017, the entire contents of which are incorporated herein by this reference.

BACKGROUND OF INVENTION

1. Field of the Invention

The present invention relates to an image pickup module including a stacked element, a wiring board, and a signal cable, a fabrication method for the image pickup module including the stacked element, the wiring board, and the signal cable, and an endoscope including the image pickup module that includes the stacked element, the wiring board, and the signal cable.

2. Description of the Related Art

An image pickup signal outputted by an image pickup device disposed at a distal end portion of an endoscope is subjected to primary processing by an electronic part mounted to a wiring board adjacent to the image pickup device.

Japanese Patent Application Laid-Open Publication No. 2005-334509 discloses an endoscope configured to transmit an image pickup signal on which primary processing is performed by an electronic part mounted to a wiring board to which a lead of an image pickup device is bonded by soldering via a signal cable bonded to the wiring board.

To accommodate a plurality of semiconductor elements in a small space and also to reduce a parasitic capacitance caused by wiring, Japanese Patent Application Laid-Open Publication No. 2013-30593 discloses a stacked element in which the plurality of semiconductor elements are stacked on one another, and penetration wirings of adjacent and facing semiconductor elements are bonded to one another. When the stacked element is used, downsizing and advanced functions of an image pickup module can be realized as compared with an imaging module in which an electronic part is mounted to a wiring board.

It is not easy to bond the signal cable to an external electrode of the stacked element. For this reason, the signal cable is connected to the external electrode of the stacked element via the wiring board.

SUMMARY OF THE INVENTION

An image pickup module according to an embodiment includes a stacked element including a light receiving surface, a rear surface on a reverse side of the light receiving surface, a plurality of semiconductor elements including an image pickup device which are stacked and bonded to one another by a plurality of element bonding sections, and an external electrode disposed on the rear surface, a first wiring board including a first main surface, a second main surface on a reverse side of the first main surface, a front electrode that is connected to the external electrode of the stacked element by an interconnecting bonding section and disposed on the first main surface, and a first electrode that is electrically connected to the front electrode and disposed on the first main surface or the second main surface, and a first signal cable connected to the first electrode of the first wiring board by a cable bonding section, in which the external electrode of the stacked element is disposed only in a second region out of a first region and the second region which are obtained by dividing the rear surface into two regions, the first wiring board is flexible and includes a bent section in a space defined by extending the first region in an optical axis direction, and a length of the first wiring board from the interconnecting bonding section on the first main surface to the cable bonding section is longer than a length of the stacked element from the interconnecting bonding section on the rear surface to an end side in the first region.

A fabrication method for an image pickup module according to an embodiment includes fabricating a stacked element including a light receiving surface, a rear surface on a reverse side of the light receiving surface, a plurality of semiconductor elements including an image pickup device which are stacked and bonded to one another by a plurality of element bonding sections, and an external electrode disposed only in a second region out of a first region and the second region which are obtained by dividing the rear surface into two regions, connecting a first signal cable to a first electrode of a first wiring board having flexibility by a cable bonding section, the first wiring board including a first main surface, a second main surface on a reverse side of the first main surface, a front electrode disposed on the first main surface, and the first electrode that is electrically connected to the front electrode and disposed on the first main surface or the second main surface, connecting the external electrode of the stacked element and the front electrode of the first wiring board to each other by an interconnecting bonding section, and bending the first wiring board to establish a state in which the first wiring board is accommodated in a space defined by extending the first region in an optical axis direction, in which a length of the first wiring board from the interconnecting bonding section on the first main surface to the cable bonding section is longer than a length of the stacked element from the interconnecting bonding section on the rear surface to an end side in the first region.

An endoscope according to an embodiment includes an image pickup module, the image pickup module including a stacked element including a light receiving surface, a rear surface on a reverse side of the light receiving surface, a plurality of semiconductor elements including an image pickup device which are stacked and bonded to one another by a plurality of element bonding sections, and an external electrode disposed on the rear surface, a first wiring board including a first main surface, a second main surface on a reverse side of the first main surface, a front electrode that is connected to the external electrode of the stacked element by an interconnecting bonding section and disposed on the first main surface, and a first electrode that is electrically connected to the front electrode and disposed on the first main surface or the second main surface, and a first signal cable connected to the first electrode of the first wiring board by a cable bonding section, in which the external electrode of the stacked element is disposed only in a second region out of a first region and the second region which are obtained by dividing the rear surface into two regions, the first wiring board is flexible and includes a bent section in a space defined by extending the first region in an optical axis direction, and a length of the first wiring board from the interconnecting bonding section on the first main surface to the cable bonding section is longer than a length of the stacked element from the interconnecting bonding section on the rear surface to an end side in the first region.

DETAILED DESCRIPTION OF THE PREFERRED EMBODIMENT(S)

First Embodiment

Figure 9:
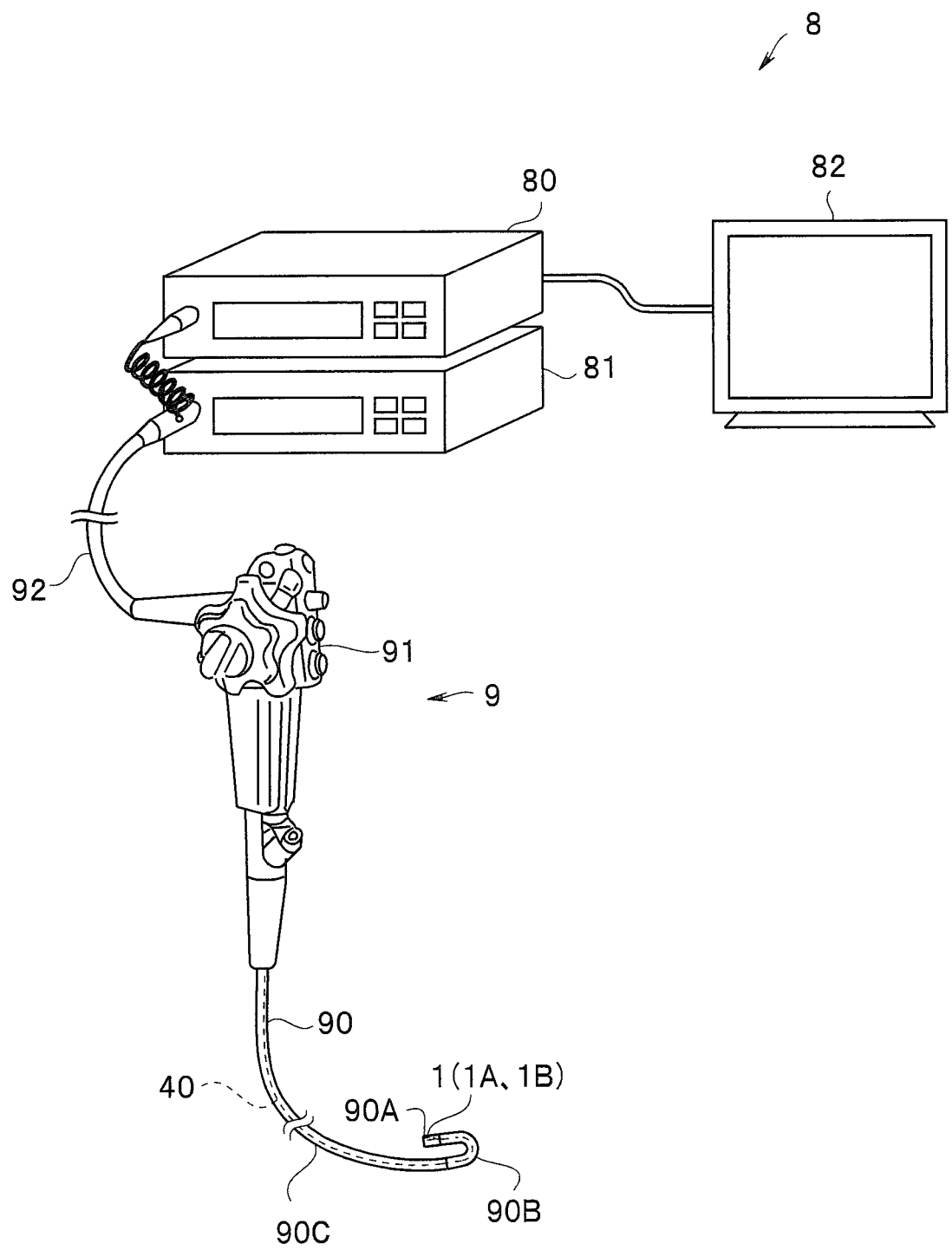
FIG. 9 is a perspective view of an endoscope system including an endoscope according to a second embodiment.

An image pickup module 1 according to an embodiment is disposed at a distal end portion 90A of an endoscope 9 (see FIG. 9).

Figure 1:
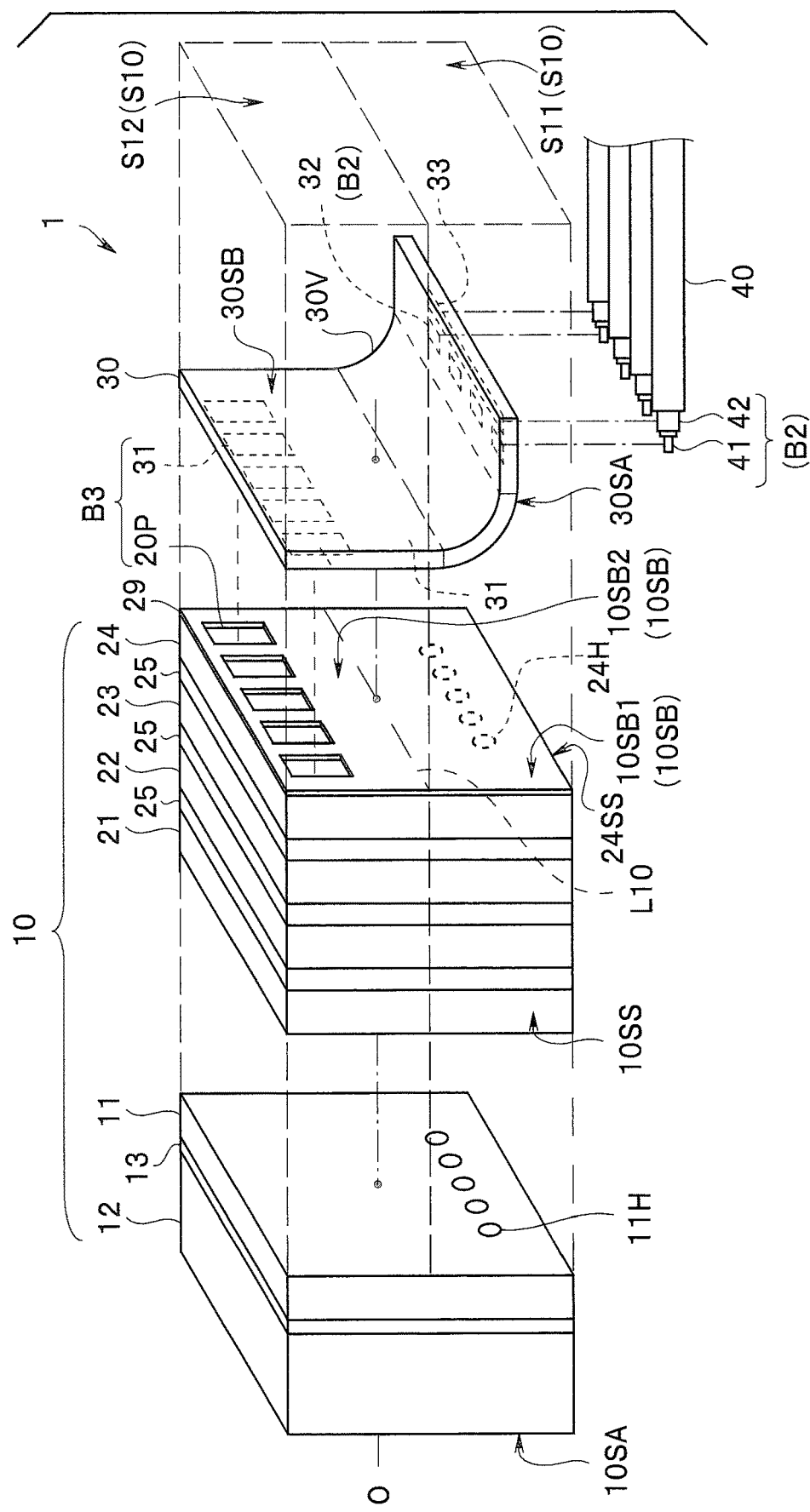
FIG. 1 is an exploded view of an image pickup module according to a first embodiment.
Figure 2:
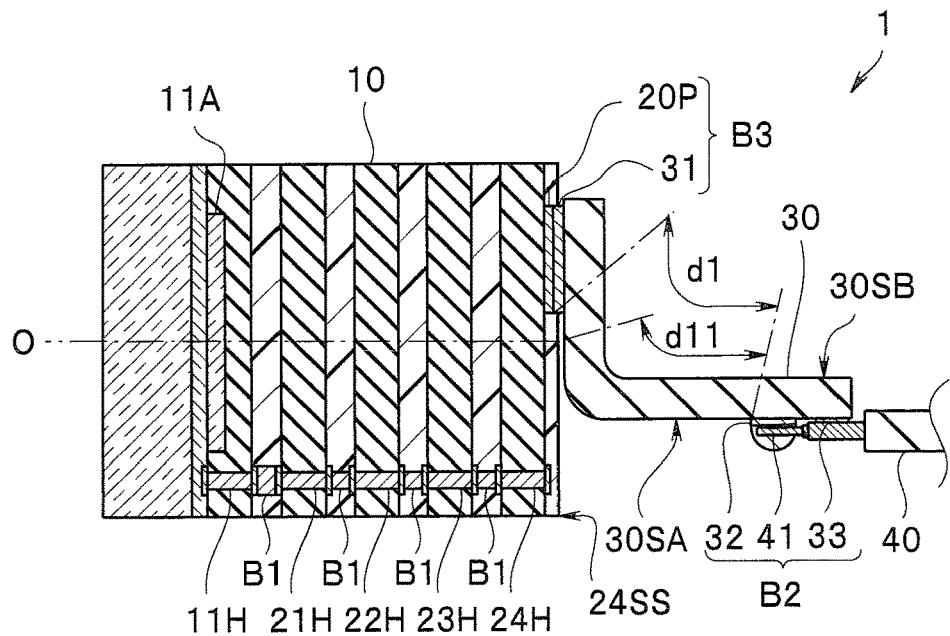
FIG. 2 is a cross sectional view of the image pickup module according to the first embodiment.

As illustrated in FIG. 1 and FIG. 2, the image pickup module 1 includes a semiconductor stacked element (hereinafter, referred to as a "stacked element") 10, a first wiring board 30, and a first signal cable 40.

Note that in the following descriptions, drawings based on respective embodiments are schematic drawings and a relationship between a thickness and a width of each of sections, a thickness ratio, a relative angle, and the like of each of the sections are different from actual configurations, and a part where a mutual dimensional relationship or ratio is different between mutual drawings may be included in some cases. Illustration of part of components and assignment of reference signs may be omitted in some cases. An object direction is referred to as a forward direction.

The stacked element 10 includes a light receiving surface 10SA, a rear surface 10SB on a reverse side of the light receiving surface 10SA, and four side surfaces 10SS.

A cover glass 12 is joined by an adhesive layer 13 to a furthest forward surface of the stacked element 10 in which an image pickup device 11 and a plurality of semiconductor elements 21 to 24 are stacked on one another. Note that the image pickup device 11 is also a semiconductor element. In other words, the stacked element 10 is a stacked body of a plurality of semiconductor elements 11 and 21 to 24 including the image pickup device 11. The cover glass 12 is not an essential component of the image pickup module 1. On the contrary, as will be described below, an image pickup optical unit 50 (see FIG. 8) constituted by a plurality of optical elements may be disposed in front of the stacked element 10.

The image pickup device 11 includes light receiving units 11A constituted by CCD or CMOS image pickup units, and the light receiving units 11A are connected to penetration wirings 11H. The image pickup device 11 may be one of a front-side illumination type image sensor and a back-side illumination type image sensor.

The image pickup device 11 and the plurality of semiconductor elements 21 to 24 constitute the stacked element 10 when adjacent semiconductor elements are stacked on one another in a state in which sealing resin 25 is sandwiched between the adjacent semiconductor elements.

The semiconductor elements 21 to 24 perform primary processing on an image pickup signal outputted by the image pickup device 11 and perform processing a control signal for controlling the image pickup device 11. For example, the semiconductor elements 21 to 24 include an analog-to-digital conversion circuit, a memory, a transmission output circuit, a filter circuit, a thin film capacitor, a thin film resistance, and a thin film inductor. The number of elements included in the stacked element 10 is, for example, 3 or higher and 10 or lower inclusive of the image pickup device 11.

The image pickup device 11 and the plurality of semiconductor elements 21 to 24 respectively include penetration wirings 11H and 21H to 24H and are electrically connected to one another by a plurality of element bonding sections B1.

The element bonding section B1 is, for example, a soldering bonding section composed of first soldering a fusing point of which is MP1. The first soldering is a soldering bump based on an electro-plating method or a soldering paste film based on printing or the like.

Figure 3:
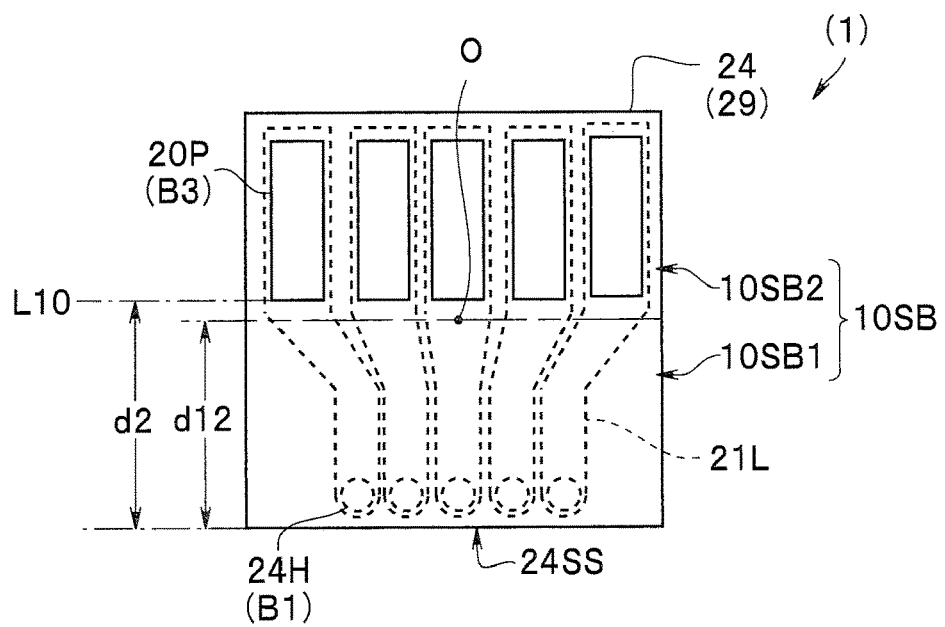
FIG. 3 is a rear view of a stacked element of the image pickup module according to the first embodiment.

A plurality of external electrodes 20P are disposed on the rear surface 10SB (rear surface of the semiconductor element 24 stacked in a furthest rearward section) of the stacked element 10. As illustrated in FIG. 3, the external electrode 20P and the penetration wiring 24H (element bonding section B1) of the semiconductor element 24 are connected to each other via an element wiring pattern 21L disposed on the rear surface 10SB. The external electrode 20P is a convex electrode constituted by a barrier Ni layer and an Au layer disposed on the element wiring pattern 21L made of Cu.

An insulating layer 29 functioning as a cover layer is disposed on the rear surface 10SB. The element wiring pattern 21L exposed from a bottom surface of an opening of the insulating layer 29 may be the external electrode 20P.

The external electrode 20P is electrically connected to a front electrode 31 of the first wiring board 30 by an interconnecting bonding section B3. An alignment mark for alignment with the first wiring board 30 may be formed on the rear surface 10SB of the stacked element 10.

The interconnecting bonding section B3 is, for example, an ultrasound bonding section. In other words, the interconnecting bonding section B3 is an interface between the external electrode 20P and the front electrode 31. The interconnecting bonding section B3 may also be a thermal ultrasound bonding section where heat is applied together with ultrasound application.

As illustrated in FIG. 3, with regard to the image pickup module 1, all of the plurality of element bonding sections B1 are disposed only inside a first space S11 defined by extending a first region 10SB1 in an optical axis direction out of the first region 10SB1 and a second region 10SB2 which are obtained by dividing the rear surface 10SB into two regions by a parting line L10, and all of the plurality of external electrodes 20P are disposed only in the second region 10SB2.

In other words, in FIG. 3, the plurality of element bonding sections B1 are disposed in columns only in a bottom side of the semiconductor elements 11 and 21 to 24, and the plurality of external electrodes 20P are disposed in columns only in a top side opposite to the disposal locations of the element bonding sections B1 across the parting line L10. The element bonding sections B1 and the external electrodes 20P are disposed in separate locations.

The first wiring board 30 includes a first main surface 30SA and a second main surface 30SB on a reverse side of the first main surface 30SA. On the first main surface 30SA of the first wiring board 30, the front electrode 31 is disposed in a front section, and a first electrode 32 connected to the front electrode 31 via an interconnecting wiring pattern (not illustrated) is disposed in a rear section. Note that the first electrode 32 may be disposed on the second main surface 30SB. In other words, it is sufficient that the first electrode 32 is disposed on the first main surface 30SA or the second main surface 30SB. An electronic part such as a chip capacitor may be mounted to the first wiring board 30. The first wiring board 30 is an inexpensive one-sided wiring board, but a double-sided wiring board or a multilayer wiring board may also be used.

The first wiring board 30 is a flexible wiring board where polyimide or the like is used as a base substance, in which the front section where the front electrode 31 is disposed is arranged in parallel with the rear surface 10SB of the stacked element 10, but the rear section where the first electrode 32 is disposed is arranged substantially in parallel with the optical axis O by a bent section 30V that is bent in a state of being spaced apart with respect to an optical axis O. In other words, a flexion angle of the bent section 30V is approximately 90 degrees.

The first electrode 32 of the first wiring board 30 is electrically connected to the first signal cable 40 by a cable bonding section B2. The cable bonding section B2 is a soldering bonding section composed of second soldering.

The first signal cable 40 is a shielding cable including core wires 41 and shielding wires 42. The plurality of core wires 41 are respectively bonded to the first electrodes 32, and the plurality of shielding wires 42 are bonded to a third electrode 33 functioning as a single common grounding potential electrode, for example.

In the image pickup module 1, the first signal cable 40 is not directly bonded to the stacked element 10. In other words, the first signal cable 40 is bonded to the first wiring board 30, and the first wiring board 30 is bonded to the stacked element 10. In other words, the first wiring board 30 is a relay board. In the image pickup module 1, even when the stacked element 10 having a small area of the rear surface 10SB is used, restrictions based on a number and an external diameter of the first signal cables 40 and connection difficulty are alleviated.

In the stacked element 10, the external electrode 20P of the interconnecting bonding section B3 is disposed in a location away from the element bonding section B1. For this reason, load, vibration, and heat applied when ultrasound bonding of the front electrode 31 to the external electrode 20P is performed are not directly transmitted to the element bonding section B1. For this reason, the image pickup module 1 has high reliability since there is no danger of damaging the stacked element 10 when the ultrasound bonding is performed.

Note that even when the element bonding section B1 is, for example, a hybrid bonding section in which an insulating film and a conductive film formed on a same surface are mutually directly bonded to each other, which is not a soldering bonding section, since load and vibration applied when ultrasound bonding of the interconnecting bonding section B3 is performed are not directly transmitted to the element bonding section B1, there is no danger of damaging the stacked element 10.

The bent section 30V of the first wiring board 30 exists inside the first space S11 in a space S10 defined by extending the light receiving surface 10SA (rear surface 10SB) in the optical axis direction. In other words, the bent section 30V exists in a location away from the optical axis O.

When the stacked element and the signal cable are connected to each other while the wiring board is sandwiched, a length of the image pickup module in the optical axis direction is lengthened. In the endoscope including the image pickup module at the rigid distal end portion, a length of the distal end portion is lengthened.

In contrast, the length of the image pickup module 1 in the optical axis direction is short. In the endoscope including the image pickup module 1 at the rigid distal end portion, the length of the distal end portion is short.

As illustrated in FIG. 2 and FIG. 3, a length d1 of the first wiring board 30 from the interconnecting bonding section B3 to the cable bonding section B2 is longer than a length d2 of the stacked element 10 from the interconnecting bonding section B3 on the rear surface 10SB to an end side (outer side) 24SS in the first region 10SB1. In other words, a length d11 of the first wiring board 30 from the optical axis O on the first main surface 30SA to the first electrode 32 is longer than a length d12 of the stacked element 10 from the optical axis O on the rear surface 10SB to the end side 24SS in the first region 10SB1.

As will be described below, in the image pickup module 1, when the front electrode 31 of the first wiring board 30 to which the first signal cable 40 is bonded is bonded to the external electrode 20P of the stacked element 10, the first wiring board 30 does not need to be bent. For this reason, it is easy to certainly bond the front electrode 31 and the external electrode 20P to each other in the image pickup module 1.

In the image pickup module 1, dimensions (external size) of the image pickup device 11 orthogonal to the optical axis O are 1 mm square or smaller, for example, 600 μm×600 μm. External sizes of the first wiring board 30 and the stacked element 10 are designed to be smaller than or equal to the external size of the image pickup device 11. In other words, the first wiring board 30 is accommodated inside the space S10 defined by extending the light receiving surface 10SA in the optical axis direction. The image pickup module 1 is an ultra-compact image pickup module specialized for an endoscope having a small diameter.

<Fabrication Method for Image Pickup Module>

Figure 4:
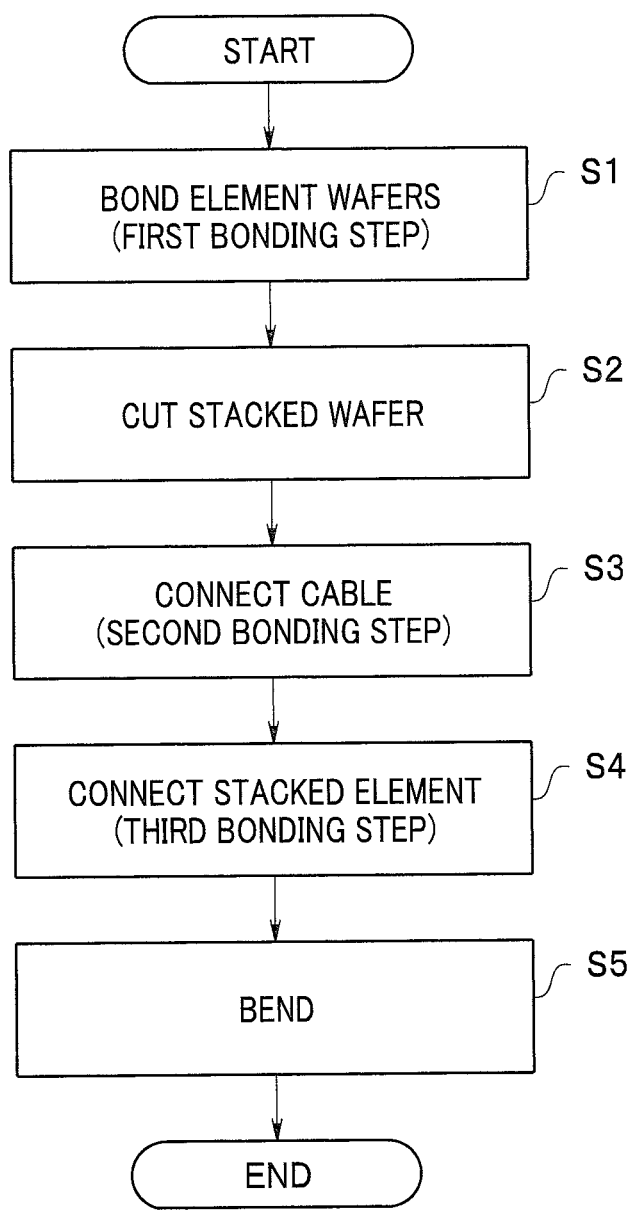
FIG. 4 is a flowchart of a fabrication method for the image pickup module according to the first embodiment.

A fabrication method for the image pickup module will be simply described along a flowchart of FIG. 4.

<Step S1> Element Wafers Bonding Step (First Bonding Step)

The stacked element 10 is fabricated by a so-called wafer level method. In other words, first, an image pickup device wafer including the image pickup device 11 and a plurality of semiconductor wafers (not illustrated) respectively including the semiconductor elements 21 to 24 are fabricated.

For example, in the image pickup device wafer, the plurality of light receiving units 11A are disposed on a silicon wafer and the like by using a related-art semiconductor fabrication technology. A peripheral circuit configured to perform primary processing on output signals of the light receiving units 11A or perform processing on drive control signals may be formed on the image pickup device wafer. A cover glass wafer that protects the light receiving units 11A is preferably joined to the image pickup device wafer from the rear surface before the penetration wirings 11H are formed.

The image pickup device wafer in which the cover glass wafer is joined by the adhesive layer 13 and the plurality of semiconductor wafers respectively including the semiconductor elements 21 to 24 are stacked on one another, and thermal processing is performed at a first temperature T1 higher than or equal to the fusing point MP1 of the first soldering in the element bonding section B1 to fabricate a stacked wafer in which the semiconductor elements 21 to 24 are electrically connected to one another. The first temperature T1 in the first bonding step is, for example, from above 200° C. to below 250° C. which is below an allowable temperature limit of the semiconductor elements 21 to 24.

The sealing resin 25 may be injected from a side surface of the stacked wafer after the bonding or may be disposed at the time of the stacking.

<Step S2> Element Wafer Cutting Step (Cutting Step)

The stacked wafer is cut to establish a state in which four side of the substantially rectangular light receiving unit 11A of the image pickup device 11 are respectively in parallel with four sides of a rectangular cross section orthogonal to the optical axis O of the stacked element into the rectangular solid stacked element 10 in pieces. The four side surfaces 10SS of the stacked element 10 fabricated by cutting the stacked wafer are cut surfaces.

Note that after the cutting into the stacked element 10 is performed, corner sections in parallel with the optical axis O may be chamfered to make cross sections in a direction orthogonal to the optical axis hexagonal, or the corner sections may be curved.

In other words, the stacked element 10 fabricated by the wafer level method is a rectangular solid but may be a substantially rectangular solid in which the corner sections are chamfered or curved.

Note that after a plurality of element wafers are cut into element chips, the first bonding step for bonding the plurality of element chips to one another may be performed to fabricate the stacked element 10.

<Step S3> Cable Connection Step (Second Bonding Step)

The first wiring board 30 where the front electrode 31 and the first electrode 32 connected to the front electrode 31 are disposed on the first main surface 30SA is fabricated.

The first signal cable 40 is electrically connected to the first electrode 32 of the first wiring board 30 by the cable bonding section B2 composed of the second soldering. A second temperature T2 in the second bonding step is a higher temperature than a fusing point MP2 of the second soldering. For example, in a case where the fusing point MP2 is from not less than 140° C. to not more than 190° C., the second temperature T2 is from above 150° C. to below 200° C.

<Step S4> Stacked Element Connection Step (Third Bonding Step)

Figure 5:
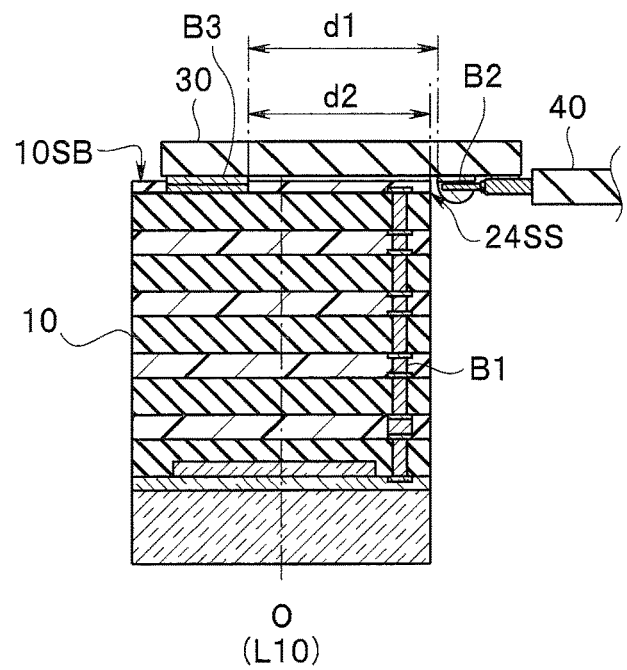
FIG. 5 is a cross sectional view for describing the fabrication method for the image pickup module according to the first embodiment.

As illustrated in FIG. 5, the front electrode 31 of the first wiring board 30 is electrically connected to the external electrode 20P of the stacked element 10 by the interconnecting bonding section B3. The interconnecting bonding section B3 is a bonding section to which a third temperature T3 is applied, for example, an ultrasound bonding section or a thermal ultrasound bonding section.

In the image pickup module 1, the length d1 of the first wiring board 30 from the interconnecting bonding section B3 to the cable bonding section B2 is longer than the length d2 of the stacked element 10 from the interconnecting bonding section B3 on the rear surface 10SB to the end side 24SS in the first region 10SB1.

For this reason, it is possible to easily perform alignment and bonding of the first wiring board 30 to which the first signal cable 40 is bonded while the first wiring board 30 is held in a flat state without being bent. In other words, since the cable bonding section B2 does not interfere with (is not in contact with) the rear surface 10SB of the stacked element 10, the first electrode 32 of the first wiring board 30 and the external electrode 20P of the stacked element 10 can be kept horizontal, and a connection defect of the interconnecting bonding section B3 can be prevented.

In the image pickup module 1 including the plurality of bonding sections, a processing temperature in the bonding processing to be performed afterward is set to be a lower temperature than a processing temperature in the previously performed bonding processing. In other words, the third temperature T3 in the third bonding step is lower than the second temperature T2 in the second bonding step, and furthermore, the second temperature T2 is lower than the first temperature T1 in the first bonding step.

<Step S5> Bending Step

Figure 6:
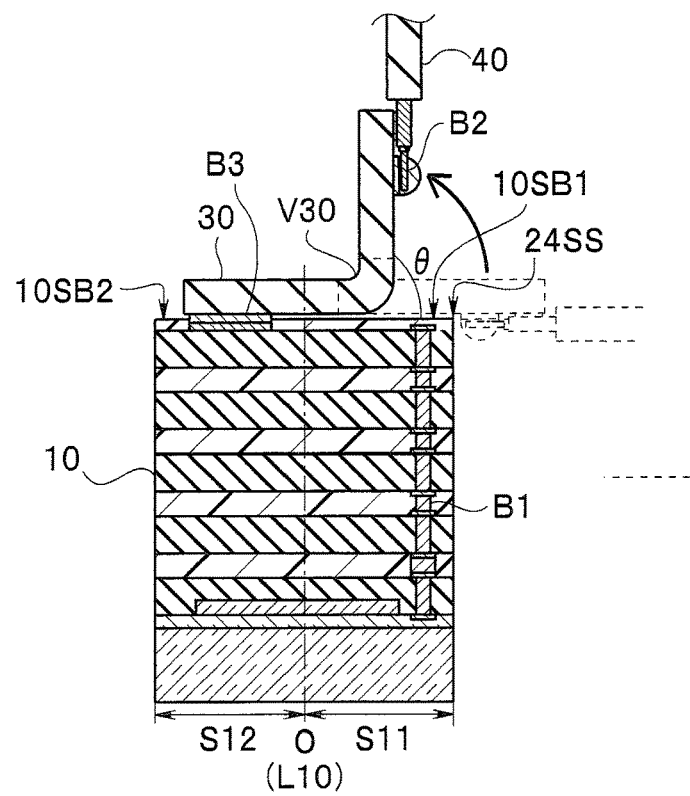
FIG. 6 is a cross sectional view for describing the fabrication method for the image pickup module according to the first embodiment.

As illustrated in FIG. 6, the first wiring board 30 is bent in the bent section 30V between the front electrode 31 and the first electrode 32. An angle θ of the bent section 30V is approximately 90 degrees, and a rear section where the first electrode 32 is arranged is arranged substantially in parallel with the optical axis O.

For this reason, the first signal cable 40 can be arranged in parallel with respect to the optical axis O without bending. Since there is no danger of application of stress caused by bending work of the first signal cable 40, the cable bonding section B2 has high reliability.

The first wiring board 30 is bent to establish a state in which the bent section 30V is located inside the first space S11 defined by extending the first region 10SB1 in the direction of the optical axis O.

In contrast, in a case where the bent section 30V is located in a second space S12 defined by extending the second region 10SB2 in the direction of the optical axis O, the length in the optical axis direction is lengthened, and also when the first wiring board 30 is bent, there is a danger of applying large stress to the interconnecting bonding section B3.

The image pickup module 1 in which the bent section 30V is located inside the first space S11 is short and small, and reliability of the interconnecting bonding section B3 is high.

As described above, in accordance with the fabrication method for the image pickup module according to the present embodiment, it is possible to obtain the small-sized, particularly, short and small image pickup module including the stacked element 10 and the first wiring board 30 and also having high performance and high reliability.

Modifications of First Embodiment

Since image pickup modules 1A and 1B according to modifications of the first embodiment are similar to the image pickup module 1 and have same advantages, components having same functions are assigned with same reference signs, and descriptions of the above-mentioned components are omitted.

First Modification of First Embodiment

Figure 7:
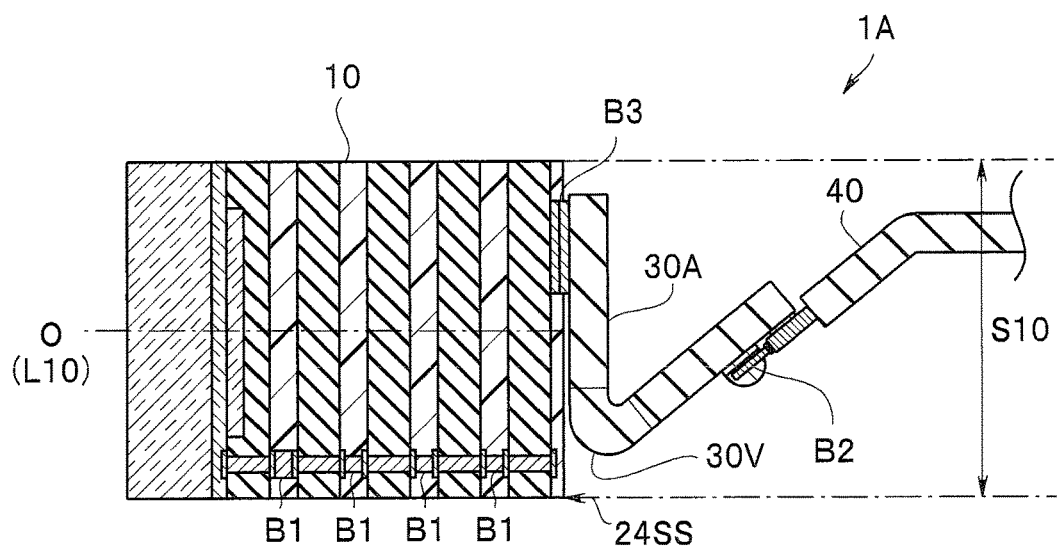
FIG. 7 is a cross sectional view of the image pickup module according to a first modification of the first embodiment.

As illustrated in FIG. 7, a first wiring board 30A of the image pickup module 1A according to the present modification is bent such that the bent section 30V has a shape having an angle at over 90 degrees.

Since the first signal cable 40 is bent, and a rear section of the first signal cable 40 extends in the direction parallel with the optical axis O, a distal end portion of the first signal cable 40 is accommodated inside the space S10 defined by extending the stacked element 10 (light receiving surface 10SA) in the optical axis direction.

In other words, in a case where the first signal cable 40 is easily bent, a bending angle of the bent section 30V is not limited to approximately 90 degrees. However, when stress application to the cable bonding section B2 is taken into account, the bending angle is preferably approximately 90 degrees like the image pickup module 1.

Second Modification of First Embodiment

Figure 8:
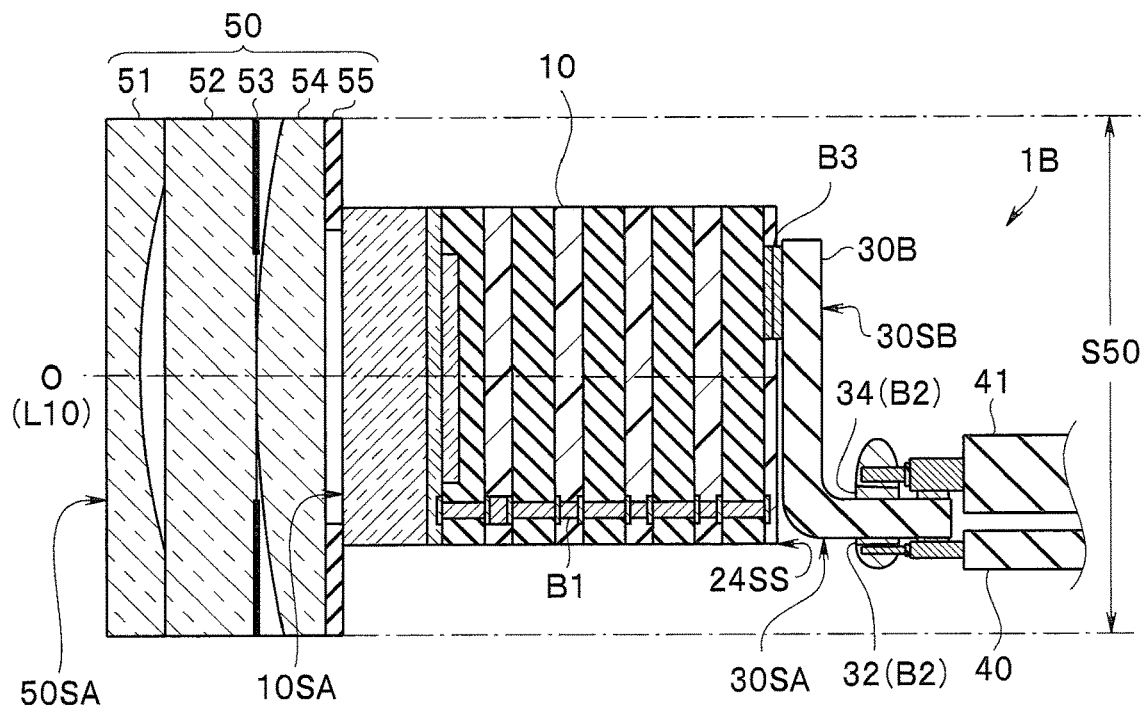
FIG. 8 is a cross sectional view of the image pickup module according to a second modification of the first embodiment.

As illustrated in FIG. 8, a first wiring board 30B of the image pickup module 1B according to the present modification is a double-sided wiring board including a second electrode 34 connected to the front electrode 31 at a rear portion of the second main surface 30SB. The image pickup module 1B further includes a second signal cable 41 bonded to the second electrode 34.

An external diameter of the second signal cable 41 is larger than the external diameter of the first signal cable 40. The second signal cable 41 is bonded to the second main surface 30SB on an optical axis side with respect to the first main surface 30SA to which the first signal cable 40 is bonded. For this reason, the external dimensions of the image pickup module 1B in the direction orthogonal to the optical axis are not increased by the thick second signal cable 41.

The image pickup module 1B further includes the image pickup optical unit 50 configured to focus light incident from an incidence surface 50SA. The image pickup optical unit 50 including a plurality of optical members 51 to 55 is disposed in front of the stacked element 10. The optical members 51 and 54 are lenses, the optical member 52 is a filter, the optical member 53 is an optical aperture, and the optical member 55 is a spacer. A number, an arrangement, and the like of the optical members are set in accordance with a specification of the image pickup optical unit.

However, to efficiently fabricate the ultra-compact image pickup module, the image pickup optical unit is preferably fabricated by cutting a stacked optical wafer in which a plurality of optical wafers respectively including a plurality of optical members are stacked on one another as in the stacked element. A side surface of the image pickup optical unit fabricated by the cutting of the stacked optical wafer is a cut surface.

An external size (external diameter) of the image pickup optical unit 50 in the direction orthogonal to the optical axis is larger than an external size (external diameter) of the stacked element 10 in the direction orthogonal to the optical axis. In the image pickup module 1B, distal end portions of the first signal cable 40 and the second signal cable 41 are arranged in a space S50 defined by extending the incidence surface 50SA in the optical axis direction.

In other words, when the thick second signal cable 41 is bonded to the first electrode 32 on the first main surface 30SA on an outer side, even in a case where the distal end portion of the second signal cable 41 is not accommodated in the space S50, and the external size of the image pickup module is increased, it is possible to prevent increase in the external size of the image pickup module when the second signal cable 41 is bonded to the second electrode 34 on the second main surface 30SB on an inner side.

Second Embodiment

As illustrated in FIG. 9, an endoscope system 8 including the endoscope 9 according to the present embodiment includes the endoscope 9, a processor 80, a light source device 81, and a monitor 82. The endoscope 9 includes an insertion section 90, an operation section 91, and a universal code 92. The endoscope 9 outputs an image signal when the insertion section 90 is inserted into a body cavity of a subject and shoots an image of an inside of the subject.

The insertion section 90 is constituted by the distal end portion 90A where the image pickup module 1, 1A, or 1B (hereinafter, referred to as the image pickup module 1 or the like) is disposed, a freely bendable bending portion 90B communicatively disposed on a proximal end side of the distal end portion 90A, and a flexible portion 90C communicatively disposed on a proximal end side of the bending portion 90B. The bending portion 90B bends by an operation of the operation section 91. Note that the endoscope 9 may be a rigid endoscope, and use of the endoscope 9 may be medical use or industrial use.

The operation section 91 where various types of buttons for operating the endoscope 9 are provided is disposed on a proximal end side of the insertion section 90 of the endoscope 9.

The light source device 81 includes a white LED, for example. Illumination light outputted by the light source device 81 is guided to the distal end portion 90A via a light guide (not illustrated) inserted through the universal code 92 and the insertion section 90 to illuminate the object.

The endoscope 9 includes the insertion section 90, the operation section 91, and the universal code 92, an image pickup signal outputted by the image pickup module 1 or the like disposed at the distal end portion 90A of the insertion section 90 is transmitted by the first signal cable 40 inserted through the insertion section 90.

Since the external size of the image pickup module 1 in the direction orthogonal to the optical axis is small, the distal end portion 90A of the insertion section 90 has a narrow diameter in the endoscope 9. Since the length of the image pickup module 1 in the optical axis direction is short, the distal end portion 90A is short and small in the endoscope 9. For this reason, the endoscope 9 is less invasive. Since the image pickup module 1 performs the primary processing on the image pickup signal outputted by the image pickup device by the stacked element 10 arranged immediately proximal to the image pickup device, the endoscope 9 displays a high quality image. Since reliability of the image pickup module 1 is high, reliability of the endoscope 9 is high.

The present invention is not limited to the above-mentioned embodiments and the like, and various modifications, alterations, and the like can be made in a range without changing the gist of the present invention.

What is claimed is:

1. An image pickup module comprising:
   a stacked element including a light receiving surface, a rear surface on a reverse side of the light receiving surface, a plurality of semiconductor elements including an image pickup device which are stacked and bonded to one another by a plurality of element bonding sections, and an external electrode disposed on the rear surface;

a first wiring board including a first main surface, a second main surface on a reverse side of the first main surface, a front electrode that is connected to the external electrode of the stacked element by an interconnecting bonding section and disposed on the first main surface, and a first electrode that is electrically connected to the front electrode and disposed on the first main surface or the second main surface; and a first signal cable connected to the first electrode of the first wiring board by a cable bonding section, wherein the external electrode of the stacked element is disposed only in a second region out of a first region and the second region which are obtained by dividing the rear surface into two regions, the first wiring board is flexible and includes a bent section in a space defined by extending the first region in an optical axis direction, and a length of the first wiring board from the interconnecting bonding section on the first main surface to the cable bonding section is longer than a length of the stacked element from the interconnecting bonding section on the rear surface to an end side in the first region.

2. The image pickup module according to claim 1, wherein a rear section where the first electrode of the first wiring board is arranged is arranged substantially in parallel with an optical axis.

3. The image pickup module according to claim 1, wherein the plurality of element bonding sections of the stacked element are arranged in a space defined by extending the first region in the optical axis direction.

4. The image pickup module according to claim 1, further comprising:

a second signal cable having an external diameter larger than an external diameter of the first signal cable, wherein the first wiring board includes a second electrode electrically connected to the front electrode on the second main surface, and the second signal cable is bonded to the second electrode.

5. The image pickup module according to claim 4, wherein an image pickup optical unit including a plurality of optical members configured to focus light incident from an incidence surface is disposed in front of the stacked element, and distal end portions of the first signal cable and the second signal cable are arranged in a space defined by extending the incidence surface in the optical axis direction.

6. A fabrication method for an image pickup module, the fabrication method comprising:

fabricating a stacked element including a light receiving surface, a rear surface on a reverse side of the light receiving surface, a plurality of semiconductor elements including an image pickup device which are stacked and bonded to one another by a plurality of element bonding sections, and an external electrode disposed only in a second region out of a first region and the second region which are obtained by dividing the rear surface into two regions;

connecting a first signal cable to a first electrode of a first wiring board having flexibility by a cable bonding section, the first wiring board including a first main surface, a second main surface on a reverse side of the first main surface, a front electrode disposed on the first main surface, and the first electrode that is electrically connected to the front electrode and disposed on the first main surface or the second main surface;

connecting the external electrode of the stacked element and the front electrode of the first wiring board to each other by an interconnecting bonding section; and bending the first wiring board to establish a state in which the first wiring board is accommodated in a space defined by extending the first region in an optical axis direction, wherein a length of the first wiring board from the interconnecting bonding section on the first main surface to the cable bonding section is longer than a length of the stacked element from the interconnecting bonding section on the rear surface to an end side in the first region.

7. The fabrication method for the image pickup module according to claim 6, wherein the bending includes arranging a rear section where the first electrode of the first wiring board is arranged, substantially in parallel with an optical axis.

8. The fabrication method for the image pickup module according to claim 6, wherein the first wiring board includes a second electrode electrically connected to the front electrode on the second main surface, and a second signal cable having an external diameter larger than an external diameter of the first signal cable is bonded to the second electrode on the second main surface.

9. An endoscope comprising an image pickup module, the image pickup module including:

a stacked element including a light receiving surface, a rear surface on a reverse side of the light receiving surface, a plurality of semiconductor elements including an image pickup device which are stacked and bonded to one another by a plurality of element bonding sections, and an external electrode disposed on the rear surface;

a first wiring board including a first main surface, a second main surface on a reverse side of the first main surface, a front electrode that is connected to the external electrode of the stacked element by an interconnecting bonding section and disposed on the first main surface, and a first electrode that is electrically connected to the front electrode and disposed on the first main surface or the second main surface; and a first signal cable connected to the first electrode of the first wiring board by a cable bonding section, wherein the external electrode of the stacked element is disposed only in a second region out of a first region and the second region which are obtained by dividing the rear surface into two regions, the first wiring board is flexible and includes a bent section in a space defined by extending the first region in an optical axis direction, and a length of the first wiring board from the interconnecting bonding section on the first main surface to the cable bonding section is longer than a length of the stacked element from the interconnecting bonding section on the rear surface to an end side in the first region.

10. The endoscope according to claim 9, wherein a rear section where the first electrode of the first wiring board is arranged is arranged substantially in parallel with an optical axis.

11. The endoscope according to claim 9, wherein the plurality of element bonding sections of the stacked element are arranged in a space defined by extending the first region in the optical axis direction.

12. The endoscope according to claim 9, further comprising:
- a second signal cable having an external diameter larger than an external diameter of the first signal cable, wherein
- the first wiring board includes a second electrode electrically connected to the front electrode on the second main surface, and
- the second signal cable is bonded to the second electrode.

13. The endoscope according to claim 12, wherein
- an image pickup optical unit including a plurality of optical members configured to focus light incident from an incidence surface is disposed in front of the stacked element, and
- distal end portions of the first signal cable and the second signal cable are arranged in a space defined by extending the incidence surface in the optical axis direction.

* * * * *